United States Patent [19]
Kass et al.

[11] Patent Number: 5,876,728
[45] Date of Patent: Mar. 2, 1999

[54] NATURAL COMPOSITION EXTRACTED FROM PLANTS USED IN THE TREATMENT OF CANCER

[75] Inventors: Howard David Kass, 12646 Cumpston, Valley Village, Calif.; Arnold I. Freeman, Azor Modiin, Israel; Albert Leyva, Lenexa, Kans.

[73] Assignee: Howard David Kass, Valley Village, Calif.

[21] Appl. No.: 594,693

[22] Filed: Jan. 31, 1996

[30] Foreign Application Priority Data

Feb. 15, 1995 [IL] Israel ......................................... 112654
Jan. 16, 1996 [IL] Israel ......................................... 116766

[51] Int. Cl.⁶ .................................................. A61K 35/78
[52] U.S. Cl. ........................ 424/195.1; 426/531; 426/655
[58] Field of Search ........................ 424/195.1; 426/531, 426/655

[56] References Cited

U.S. PATENT DOCUMENTS 3,932,628  1/1976  Hudson ................................ 424/195.1
5,362,641  11/1994 Fuks et al. ............................. 435/209
5,378,465  1/1995  Zeines ................................... 424/195.1

OTHER PUBLICATIONS

The Merck Index, Tenth Edition, Merck & Co., Inc. 1983, pp. 244, 274, 506, 690, 794, 795, 908, and 1202.
The Peterson Field Guide Series, A Field Guide to Medicinal Plants, Eastern and Central North America, Houghton Mifflin Company, Boston, pp. 50, 144, 200, and 240, 1990.
Alternative Medicine, The Definitive Guide, James Strohecker, Ed., Future Medicine Publishing, Inc. Washington, pp. 515 and 516, 1994.

*Primary Examiner*—David M. Naff
*Assistant Examiner*—Janet M. Kerr
*Attorney, Agent, or Firm*—Browdy and Neimark

[57] ABSTRACT

The invention is a method of treating cancer comprising administering an effective amount of either a composition of three herbal extracts consisting essentially of 30% to 70% by weight Goldenseal, 20% to 40% by weight of Myrtle, and 5% to 20% by weight of Centaurea, or a composition of seven herbal extracts consisting essentially of 3% to 5% by weight Centaurea, 1.5% to 4% by weight Capsicum, 1.5% to 4% by weight Lobelia, 20% to 40% by weight Myrrh, 30% to 50% by weight Echinacea, 15% to 25% by weight Goldenseal, and 3% to 5% by weight Myrtle. The compositions were prepared by separately extracting each herb by mixing the herb in water, ethyl alcohol, or a mixture of water and ethyl ether, boiling and cooling the mixture, allowing the mixture to stand for about two weeks, filtering the mixture to obtain the liquid phase, and combining each of said extracts to obtain said compositions.

15 Claims, 3 Drawing Sheets x > 5% ** >> 5%
(LOWER THE IC50, HIGHER THE POTENCY)

NATURAL COMPOSITION EXTRACTED FROM PLANTS USED IN THE TREATMENT OF CANCER

INTRODUCTION

The present invention concerns novel compositions and their health and medical use. The present invention more particularly concerns a novel composition containing natural ingredients for use to treat a large variety of cancers.

BACKGROUND OF THE INVENTION

There are innumerable drugs which are used to combat a large variety of cancers. However, these drugs are made of individual or combinations of chemicals. While some are effective, many have side effects which prevent their long-term or recurrent use. In addition, there has been an increasing number of effective drugs which can no longer be used due to the resistance by the causative agent.

OBJECTIVES OF THE INVENTION

It is the objective of the present invention to provide a novel method of combatting cancers. It is a further objective of the present invention to provide novel pharmaceutical compositions containing no synthetic organic chemicals and having anti-cancer properties.

SUMMARY OF THE INVENTION

We have found a novel method of combatting cancer comprising ingesting and/or applying a composition prepared by extracting one or more plants selected from the group consisting of a Centaurea, Capsicum, Sambucus, Lobelia, Myrrh, Echinacea, Goldenseal, and myrtle. While extracts of one or more of these plants were found to be active against cancers immune to known anti-cancer agents, activity against cancer has also been found with the extension of specific binary and three-way mixtures of the above described plants as well as mixtures of all of the plants as will be detailed below.

Figure 1:
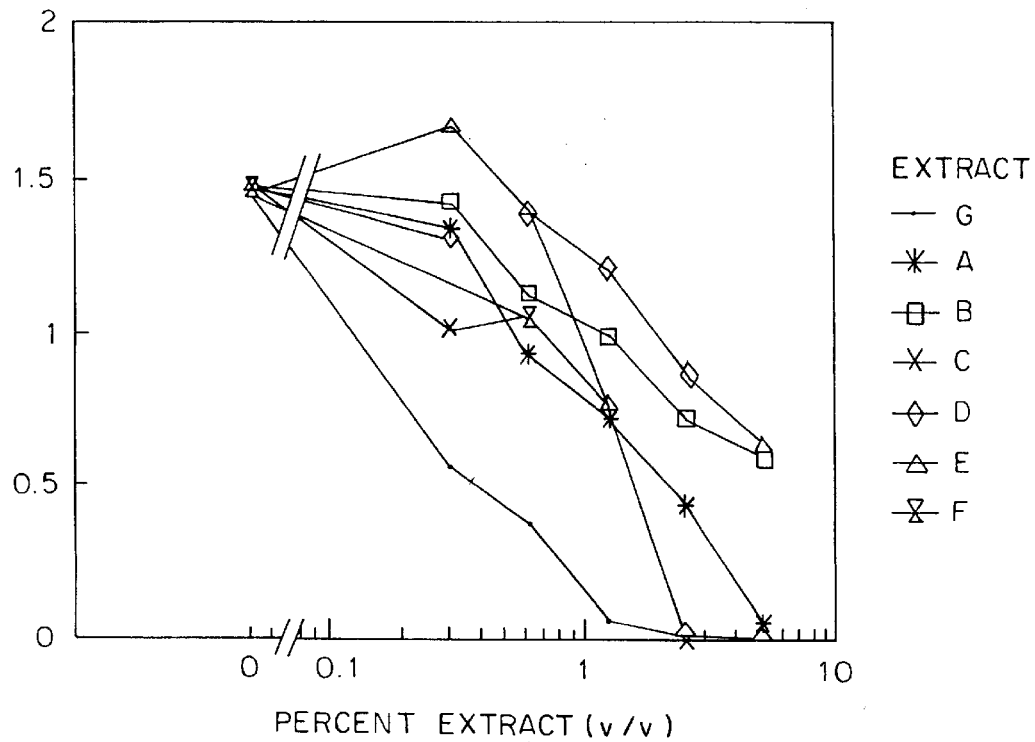
FIG. 1 shows the cytotoxic effects of plant extracts on HCT-8 colon tumor cells.

The key to extracts is as follows;

G=Goldenseal
A=Centaurea
B=Capsicum
C=Sambucus
D=Lobelia
E=Myrrh
F=Echinacea
H=Myrtle All of the figures have a y-axis printed on the upper left part of the figure, namely "Cell Growth (ABS)".

DETAILED DESCRIPTION OF THE INVENTION

Binary mixtures of Goldenseal, Myrtle, and Centaurea, when each plant is initially present in the proportion of 3:1 to 1:3 have found to be active. The plants in the referred three-way mixture are initially present in the following percentages by weight:

(a) 30% ;to 70% Goldenseal
(b) 20% to 40% Myrtle and
(c) 5% to 20% Centaurea.

Preferable initial percentages of this mixture are 35% to 65%; 25% to 35% and 7% to 15%, respectively.

The eight way mixture initially contains the following percentages by weight:

(a) 3% to 5% Centaurea
(b) 1.5% to 4% Capsicum
(c) 1.5% to 3% Sambucus
(d) 1.5% to 4% Lobelia
(e) 20% to 40% Myrrh
(f) 30% to 50% Echinacea
(g) 15% to 25% Goldenseal
(h) 3% to 5% Myrtle Preferable initial percentages of this mixture are 2% to 3%, 2% to 2.5%, 2% to 3%; 25% to 35%; 35% to 45%; 18% to 22%; and 35% to 45% respectively.

While the plants or their mixtures may be extracted with any convenient solvent, preferred solvents are water or ethyl alcohol. The novel compositions are readily prepared by adding, for example water to the dry plant or mixture of plants in a suitable container in an amount equal to approximately four times the weight of the dry mixture, bringing to a boil, boiling for a short while and adding to the cooled water solution sufficient ethyl alcohol to result in an alcohol content of the diluted solution equal to 10% to 30% ethyl alcohol by volume. The thus obtained mixture was allowed to stand for two weeks, stirring occasionally. The resulting mixture was filtered twice and bottled.

When ethyl alcohol or a mixture of water and ethyl alcohol are used as extraction liquids, there is no need for the step of adding additional alcohol. The thus obtained tincture can be used by adding directly to liquids or other foods. Alternatively, the tincture may be evaporated to form a powder, which can be mixed with foods.

The composition of the present invention in the form of extracts of the individual plants or their mixtures have shown unusual and unexpected activity against cancer cells such as colon, leukemia, and the like. Such cells were cured in at least 3 to 7 samples, even at a dilution of 200 times.

The dosage required to obtain a satisfactory response depends on the circumstances. Generally a dose of 10 to 40 drops 4 to 6 times a day is required. A preferred dose for most cases is 15 to 30 drops, with 30 drops for adults and 15 drops for children up to age 12.

While the invention will now be described in connection with certain preferred embodiments in the following examples. It will be understood that it is not intended to limit the invention to these particular embodiments. On the contrary, it is intended to cover all alternatives, modifications and equivalents as may be included within the scope of the invention as defined by the appended claims.

EXPERIMENTAL—GENERAL

Test Substances

Plant Extracts were tested for cytotoxic effects in cultured cell lines. All examples were ethanol extracts of the plant leaves with a final alcohol concentration of 16–41% (vol/vol), mean of 24%. All plant extracts were supplied in dark glass bottles and stand at room temperature.

Cell Culture

The following human cancer cell lines were used: colon (HCT8, COLO201, SW 837); lung (SW1573, SW1573-2R160). The cells were obtained commercially from ATCC, except the SW 1573 lines were obtained from Dr. H. Joenie, Free University, Amsterdam, Holland. All cell lines were maintained in liquid nitrogen storage until use. When in use for cytotoxicity testing, cells were maintained in exponential growth in plastic flasks (Falcon) in RPM1-164) medium containing 10% fetal bovine serum. All cell culture media and reagents were obtained from JRH or GIBCO.

Other chemicals were from Sigma. Cell lines grew as adherent monolayers. The adherent cultures were passaged to new flasks and fresh medium after brief (Leyva, 1990) trypsinization. SW 1573-2R160 is a variant subline of SW 1573 that is known to over express mdr-1 gene coding for P-glycoprotein-170, thus representing classical multi-drug resistance (MDR) Broxterman, 1989: Deuchars, 1989). This MDR cell line is over 100 times less sensitive to the anticancer drugs dexorubicin, vincristine, and etoposide, when compared to the parent cell line SW 1573.

Two normal human skin fibroblast lines were used and maintained as with the tumor cell lines, except alpha-MEM medium was used for maintenance culture. CMH-F1 fibroblasts were originated in our laboratory and CCD 973 fibroblast line was obtained from ATCC.

Cytotoxicity Assay

Cytotoxicity was determined by the MTT assay in multiwell plates (Pieters, 1988; Leyva, 1990). Cells were plated in 96-well microplates in RMPMI-1640 medium plus 10% fetal bovine serum supplement with antibiotics (penicillin, streptomycin, fungizone; not toxic to human cells). The number of cells plated varied for the different lines; in most cases 700–2000 cells per 100 ul per well. Plated cells were then allowed to equilibrate overnight. Plant extracts were diluted in culture medium and 100 ul added to cells. The highest concentration of plant extract tested was always 5% that resulted in an ethanol concentration of about 1%. Ethanol was tested alone and found to be 30% growth inhibitory at 1%, and not inhibitory at 0.5%. Plant extracts were usually tested at several 2-fold serial dilutes. After cells were incubated with and without added test substances for 3 days under standard culture conditions, the number of metabolically viable cells was determined by the MTT tetrazolium dye assay.

Briefly, the old medium was removed 200 ul of fresh medium with 0.5 mg/ml MTT was added. Cells were then further incubated for 3 hr. The medium was removed and the blue black MTT formazan produced by metabolically active cells was dissolved with 150 ul of dimethyl sulfoxide. Absorbance was determined at 550 nm using an ELISA plate reader (Cambridge instruments). Absorbance was plotted versus plant extract concentration (%, vol/vol) to obtain dose-response curves. Cytotoxicity was measured as the $IC_{50}$, the concentration of plant extract or test agent that produces 50% decrease in the number viable cells (MTT absorbance) compared to untreated controls.

Fresh Tumor Specimens

Single-cell suspensions of tumor cells were obtained from surgical specimens of patients with cancer and examined for sensitivity to test substances, as reported elsewhere (Leyva, 1993). Briefly, tissue was minced and then broken apart enzymatically and mechanically. Viable tumor cells were plated at 50,000 well in 96-well plates. Otherwise, the cytotoxicity assay was the same as for cell lines. An alternative method for small numbers of tumor cells was to plate 5,000 cells in 6-well plate in 1 ml, 0.3% agar medium (semi-solid) with and without test agent. After 3 days incubation, MTT is added for overnight to stain viable cells.

The key to the labelled extracts in the following examples are as follows:

| Label | Plant |
| --- | --- |
| A | Centaurea |
| B | Capsicum |
| C | Sambucus |
| D | Lobolia |
| E | Myrrh |
| F | Echinacea |
| G | Goldenseal |
| H | Myrtle |

EXAMPLE 2

Figure 2:
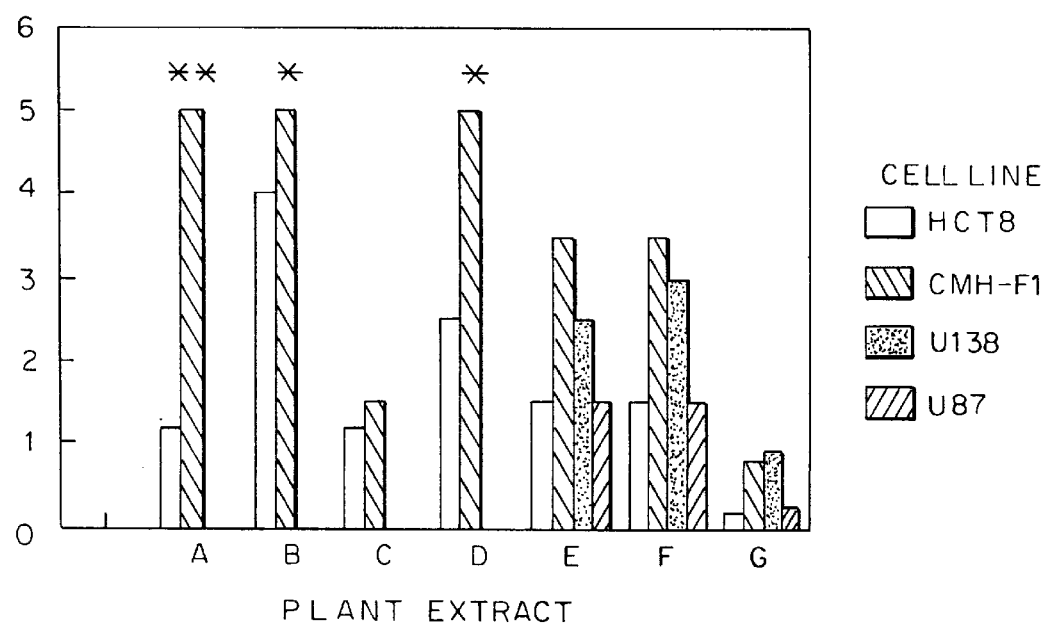
FIG. 2 shows the cytotoxicity of plant extracts in different human tumor cells and normal fibroblast cells.

FIG. 2 summarizes data from 2–3 experiments for four different cell lines including CMH-F1 fibroblasts tested for sensitivity to the various plant extracts.

EXAMPLE 3

All plant extracts were tested in at least HCT 8 tumor cells and normal fibroblasts. Plant extracts E, F and G were also tested in all 4 cell lines including U138 and U87 gliomas. Plant extract G was much less toxic to CMH-F1 fibroblasts and U138 glioma. In other recent experimental chemotherapy studies, it was found that U138 glioma cells are highly resistant to the plant derived anticancer drug etoposide. Similar results were seen for plant extracts E and F. Although plant extract A was moderately cytotoxic to HCT 8, it was exceptionally inactive against fibroblasts. Further experiments were conducted with plant extracts A, F, G and H in 2 fibroblast cell lines.

Figure 3:
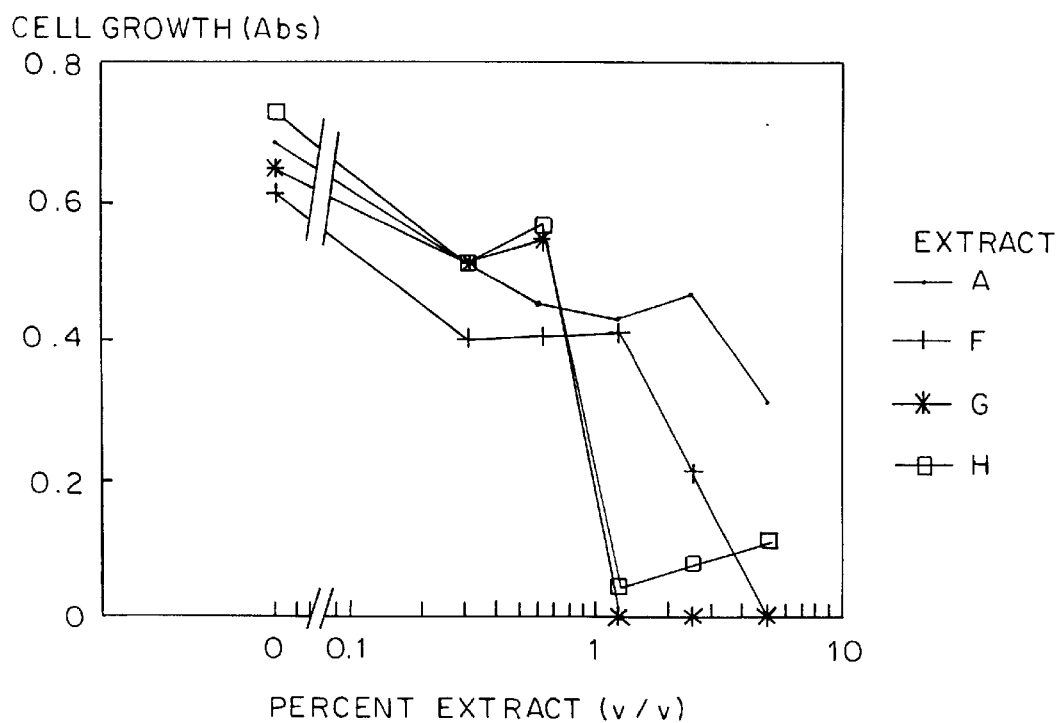
FIG. 3 shows the cytotoxicity of plant extracts in non-tumor CMH-F1 skin fibroblast cells.

FIG. 3 shows representative data for the two fibroblast lines; low sensitivities were observed for plant extracts A, F, G, and H. Plant extracts G and H were the most cytotoxic at $IC_{50}$'s of 0.6 to 0.9%. Plant extracts A and F were several fold less active.

EXAMPLE 4

Figure 4:
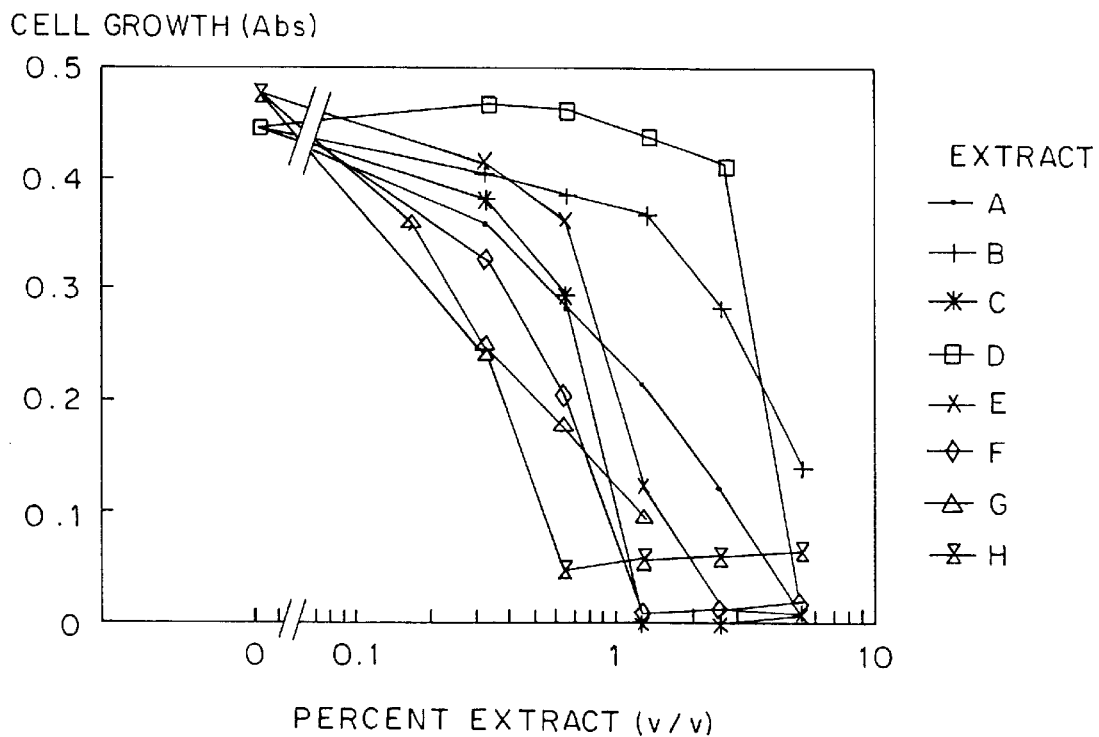
FIG. 4 shows the cytotoxic effects of plants extracts in drug sensitive SW 1573 lung cancer cells.

Plant extracts A–H were tested for cytotoxicity in SW 1573 and SW1573-2R160 to determine if the cytotoxic substances in these plant extracts are similar to those natural product drugs to which MDR tumor cells (2R160) are resistant. SW 1573 cells had a sensitivity profile for the different plant extracts similar to that of other tumor cells (FIG. 4). Plant extracts G and H were the most active at an $IC_{50}$ to 0.4%. The least active were plant extracts B and D at an $IC_{50}$ of 30%.

EXAMPLE 5

Figure 5:
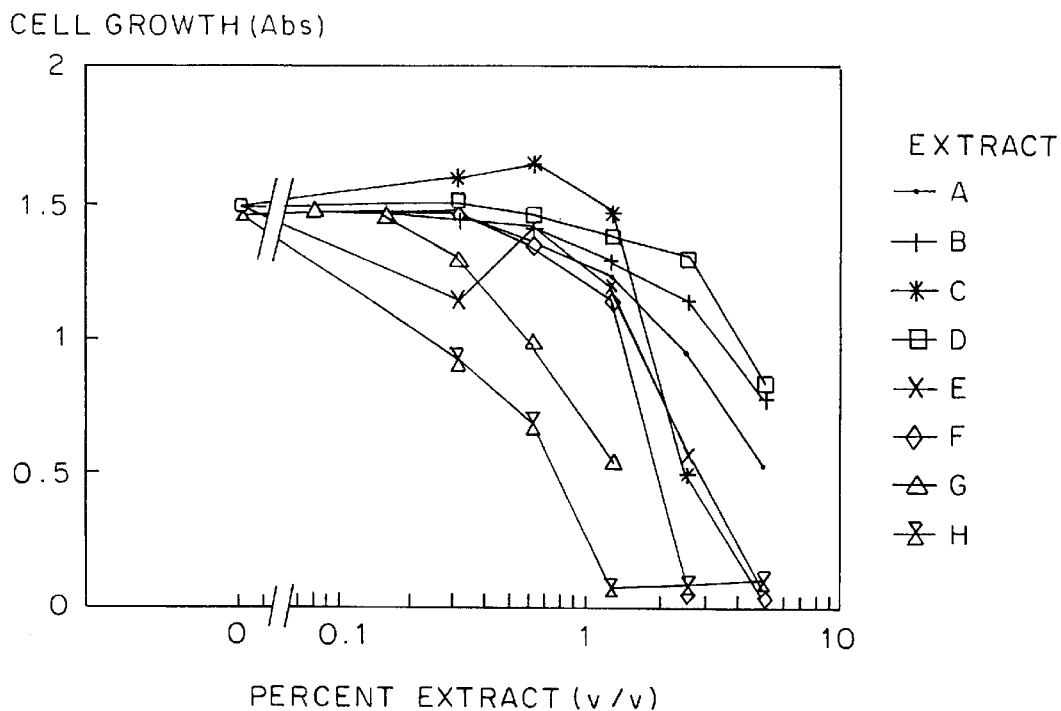
FIG. 5 shows the cytotoxic effect of plant extracts in multi-drug resistant SW 1573-2R160 lung cancer cells.

2R160 cells were less sensitive to the different plant extracts with $IC_{50}$ values 2–3 times higher (FIG. 5). Clearly, there was no evidence of drug resistance to the degree found for those natural product drugs including antibiotics, vinca alkaloids, epipodophyllotoxins, and taxol. The plant extract substances tested do not appear to be subject to expulsion from cells by the transmembrane efflux pump (mdr-1 gene product).

EXAMPLE 6

Figure 6:
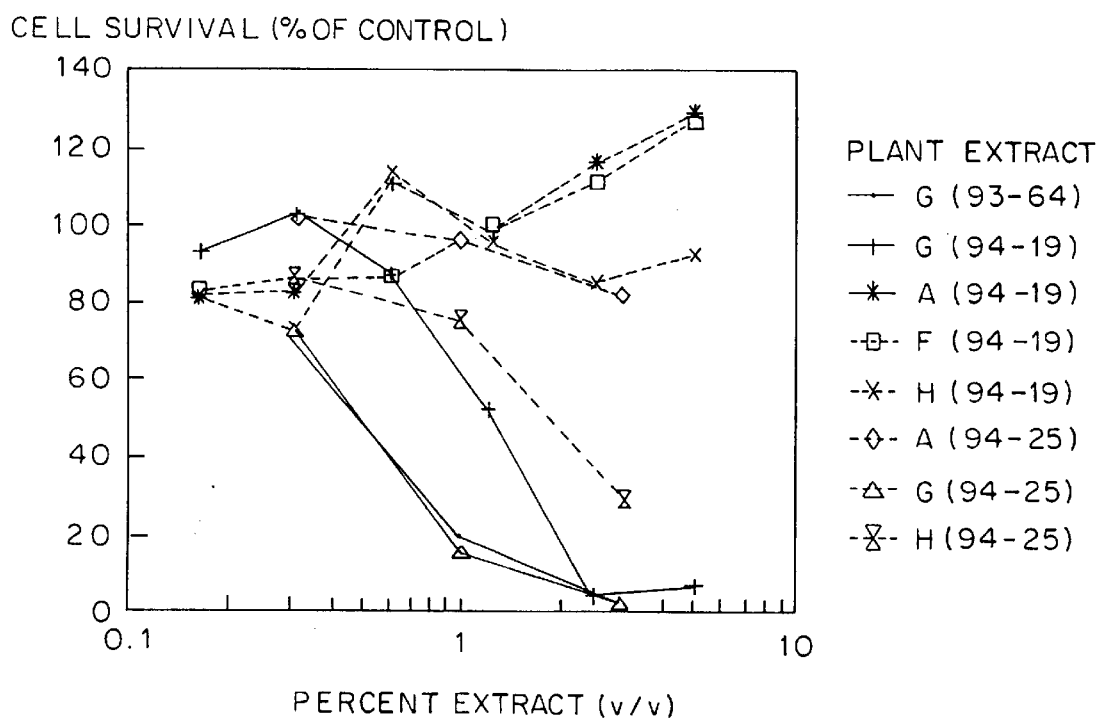
FIG. 6 shows the in vitro effects of plant extracts on fresh tumor cells derived from individual patients.

FIG. 6 shows the cytotoxic effects of plant extracts in primary cultures of two ovarian tumors (93-64 and 94-19) and one brain tumor (94-25).

EXAMPLE 7

Cytotoxic effects were studied with regard to cell survival (absorbance) expressed as % of control. Plant extract G was cytotoxic at $IC_{50}$ of 0.5 to 1.2% plant extract, levels similar to those observed for tumor cell lines. Plant extracts A, F and H were not active at concentrations as high as 5% plant extract, in most cases. Plant extract H did have modest activity against the brain tumor.

While the ovarian tumors did show sensitivity to conventional anticancer drugs (doxorubicin cisplatin, cyclophosphamide), the brain tumor appeared to be multi-drug resistant.

EXAMPLE 8

In studies on A, G and H plant extracts it was found that their cytotoxic activities are not reversed by the presence of nucleosides and thus do not involve the syntheses of purine or pyrimidine precursors of RNA or DNA. Also, extract A, but not G or H, was more potent in cells with depiction of glutathione, a major detoxifying agent in all cells.

EXAMPLE 9

In a study of G and H it was demonstrated that both caused DNA damage as determined by a fluorescence procedure reported by Kanter and Schwarz (Mol. Pharmacol., 22;145–151, 1982). The effects were dose dependent after a 24-hour exposure period. Positive control used in these essays was etoposide. This can account for the cytotoxic as well cytostatic effect on tumor cells in vitro.

EXAMPLE 10

Finally, plant extract G has been fractionated by a C18 reverse phase column using a 20% to 80% methanol linear gradient (over 40 minutes). Four fractions were observed with cytotoxic activity (as determined against colon tumor cells). Three of these fractions were stable and were further tested against 3 different cell lines. Differential cytotoxicity was similar in fractions labeled X and Y, whereas fraction z was equally toxic to all 3 cell lines.

EXAMPLE 11

Fractionation of the individual extracts of A to H and further study of the individual fraction has demonstrated that these fractions were not the known cytotoxic agents such as Berberine, hydrastin, and Canadine.

EXAMPLE 12

A Limited clinical study of the extract of all eight plants in 30 patients (whose cancers did not respond to standard treatment such as chemotherapy, radiotherapy and the like) gave remissions in 8 patients (partial response). Three of those 8 had a complete remission and were not using any other form of therapy at the time of remission.

What is claimed is:

1. A method of treating cancer comprising administering to a patient in need thereof a cancer-treatment effective amount of a composition which consists essentially of:
   (a) 30% to 70% by weight of Goldenseal extract;
   (b) 20% to 40% by weight of Myrtle extract; and
   (c) 5% to 20% by weight of Centaurea extract.

2. A method in accordance with claim 1 wherein said composition consists essentially of:
   (a) 35% to 65% by weight Goldenseal extract;
   (b) 25% to 35% by weight Myrtle extract; and
   (c) 7% to 15% by weight Centaurea extract.

3. A method according to claim 2 wherein said extracts are substantially free of berberine, hydrastine and canadine.

4. A method according to claim 1 wherein said composition is a liquid further consisting essentially of water, ethyl alcohol or a mixture of water and ethyl alcohol.

5. A method of according to claim 4 wherein said composition is administered in a dosage amount of 10 to 40 drops, 4 to 6 times per day.

6. A method of treating cancer comprising administering to a patient in need thereof a cancer-treatment effective amount of a composition which consists essentially of:
   (a) 3% to 5% by weight Centaurea extract;
   (b) 1.5% to 4% by weight Capsicum extract;
   (c) 1.5% to 4% by weight Lobelia extract;
   (d) 20% to 40% by weight Myrrh extract;
   (e) 30% to 50% by weight Echinacea extract;
   (f) 15% to 25% by weight Goldenseal extract; and
   (g) 3% to 5% by weight Myrtle extract.

7. A method according to claim 6 wherein said composition consists essentially of:
   (a) 2% to 4% by weight Centaurea extract;
   (b) 2% to 3% by weight Capsicum extract;
   (c) 2% to 3% by weight Lobelia extract;
   (d) 25% to 35% by weight Myrrh extract;
   (e) 35% to 45% by weight Echinacea extract;
   (f) 18% to 22% by weight Goldenseal extract; and
   (g) 2.5% to 4.5% by weight Myrtle extract.

8. A method according to claim 6 wherein said composition is a liquid further consists essentially of water, ethyl alcohol or a mixture of water and ether alcohol.

9. A method according to claim 8 wherein said composition is administered in a dosage amount of 10 to 40 drops, 4 to 6 times per day.

10. A process for preparing a cancer treating composition consisting essentially of 30% to 70% by weight of Goldenseal extract, 20% to 40% by weight of Myrtle extract, and 5% to 20% by weight of Centaurea extract, comprising:
    preparing each extract by mixing separately each of Goldenseal, Myrtle, and Centaurea with a solvent selected from the group consisting of water, ethyl alcohol and a mixture of water and ethyl alcohol to provide a liquid phase and a solid phase;
    bringing the mixture of said liquid phase and said solid phase to a boil;
    cooling the mixture and optionally adding an amount sufficient of ethyl alcohol to the liquid phase to provide a concentration of 10–30% ethyl alcohol by volume;
    permitting the mixture to stand for at least about two weeks;
    filtering to obtain the liquid phase which constitutes said composition; and
    combining each of said extracts to obtain said composition.

11. A method according to claim 10 wherein said solvent is waster.

12. A method according to claim 10 wherein said solvent is a mixture of water and ethyl alcohol.

13. A composition obtained by the process of claim 10.

14. A process for preparing a cancer-treating composition consisting essentially of 3% to 5% by weight Centaurea extract, 1.5% to 4% by weight Capsicum extract, 1.5% to 4% by weight Lobelia extract, 20% to 40% by weight Myrrh extract, 30% to 50% by weight Echinacea extract, 15% to 25% by weight Goldenseal extract, and 3% to 5% by weight Myrtle extract, comprising:

preparing each extract by mixing separately each of Centaurea, Capsicum, Lobelia, Myrrh, Echinacea, Goldenseal, and Myrtle with a solvent selected from the group consisting of water, ethyl alcohol and a mixture of water and ethyl alcohol to provide a liquid phase and a solid phase;

bringing the mixture of said liquid phase and said solid phase to a boil;

cooling the mixtures and optionally adding an amount sufficient of ethyl alcohol to the liquid phase to provide a concentration of 10–30% ethyl alcohol by volume;

permitting the mixture to stand for at least about two weeks;

filtering to obtain the liquid phase which constitutes said composition; and combining each of said extracts to obtain said composition.

15. A composition obtained by the process of claim 14.

* * * * *